US 6,669,703 B2

(12) United States Patent
Shue

(10) Patent No.: US 6,669,703 B2
(45) Date of Patent: Dec. 30, 2003

(54) VAGINAL SUPPOSITORY DELIVERY DEVICE

(76) Inventor: Ming-Jeng Shue, No. 14, Lane 8, Chung-I St., Hsi Dist., Taichung City (TW)

( * ) Notice: Subject to any disclaimer, the term of this patent is extended or adjusted under 35 U.S.C. 154(b) by 0 days.

(21) Appl. No.: 10/078,156

(22) Filed: Feb. 20, 2002

(65) Prior Publication Data

US 2003/0158511 A1 Aug. 21, 2003

(51) Int. Cl.[7] .................. A61B 17/42; A61B 10/267; A61B 10/32; A61M 31/00
(52) U.S. Cl. .................. 606/119; 600/185; 600/201; 600/211; 604/60
(58) Field of Search ............... 604/58–65, 57, 604/16, 288, 242, 93.01, 515, 514, 218, 236, 12–17; 600/184–189, 220–246; 606/119

(56) References Cited

U.S. PATENT DOCUMENTS 5,785,648 A * 7/1998 Min ........................... 600/206
5,846,249 A * 12/1998 Thompson ................... 606/119

* cited by examiner

Primary Examiner—Manuel Mendez
Assistant Examiner—Roz Ghafoorian
(74) Attorney, Agent, or Firm—Morgan Lewis & Bockius LLP

(57) ABSTRACT

A vaginal suppository delivery device includes a pincer body having upper and lower clamp members that cooperate to confine a passage, a sleeve member, and a push rod. The clamp members have connecting and clamp end sections. The sleeve member is movable toward the connecting and clamp end sections of the clamp members so as to permit the clamp end sections to move away from and toward each other, thereby permitting a suppository to be disposed and clamped in a drug receiving groove in the passage. The push rod has an operating end that is operable so as to enable a drug pushing end to push the suppository to move out of the passage after the pincer body has been inserted into a vaginal cavity, thereby delivering the suppository into the vaginal cavity.

8 Claims, 5 Drawing Sheets

VAGINAL SUPPOSITORY DELIVERY DEVICE

BACKGROUND OF THE INVENTION

1. Field of the Invention

The invention relates to a vaginal suppository delivery device, more particularly to a vaginal suppository delivery device that is easy and convenient to use.

2. Description of the Related Art

Vaginal infections or inflammation are generally treated by drug injection, oral intake of drugs, or vaginal suppositories. Since the vaginal suppository is more effective and has little side effect, it is frequently prescribed by gynecologists to female patients.

When the suppository is delivered deep into the vagina, the suppository will be melted by secretions in the vagina so as to soak the vaginal cavity, thereby effectively treating the infection.

Normally, the suppository is pushed into the vagina with the use of fingers. However, due to the limited finger length and lack of experience, the suppository cannot be delivered into the deepest part of the vagina called Fornix, such that the effectiveness of the suppository is reduced.

SUMMARY OF THE INVENTION

Therefore, the main object of the present invention is to provide a vaginal suppository delivery device that is convenient to use and that can deliver the suppository into a proper depth of the vaginal cavity.

According to this invention, a vaginal suppository delivery device comprises a pincer body, a sleeve member, and an elongate push rod. The pincer body has upper and lower clamp members that cooperate to confine a passage extending in an axial direction. Each of the upper and lower clamp members has a clamp end section and a connecting end section opposite to the clamp end section. The upper and lower clamp members are connected to each other at the connecting end sections, and are movable toward and away from each other at the clamp end sections. The passage has a drug receiving groove formed in the clamp end sections and adapted for receiving a suppository therein. The sleeve member is sleeved slidably on the pincer body, and is movable toward the connecting end sections of the upper and lower clamp members so as to permit the clamp end sections of the upper and lower clamp members to move away from each other, thereby permitting the suppository to be disposed in the drug receiving groove. The sleeve member is further movable toward the clamp end sections of the upper and lower clamp members so as to permit the clamp end sections of the upper and lower clamp members to move toward each other, thereby clamping the suppository in the drug receiving groove. The elongate push rod is slidably extended into and is movable in the axial direction along the passage, and has a drug pushing end and an operating end opposite to the drug pushing end in the axial direction. The operating end extends through the passage at the connecting end sections of the upper and lower clamp members, and is operable so as to enable the drug pushing end to push the suppository to move out of the passage after the pincer body has been inserted into a vaginal cavity, thereby delivering the suppository into the vaginal cavity.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Referring to FIGS. 1 to 5, the preferred embodiment of a vaginal suppository delivery device according to the present invention is shown to comprise a pincer body 1, a sleeve member 2, a positioning tube 3, and an elongate push rod 4.

Figure 1:
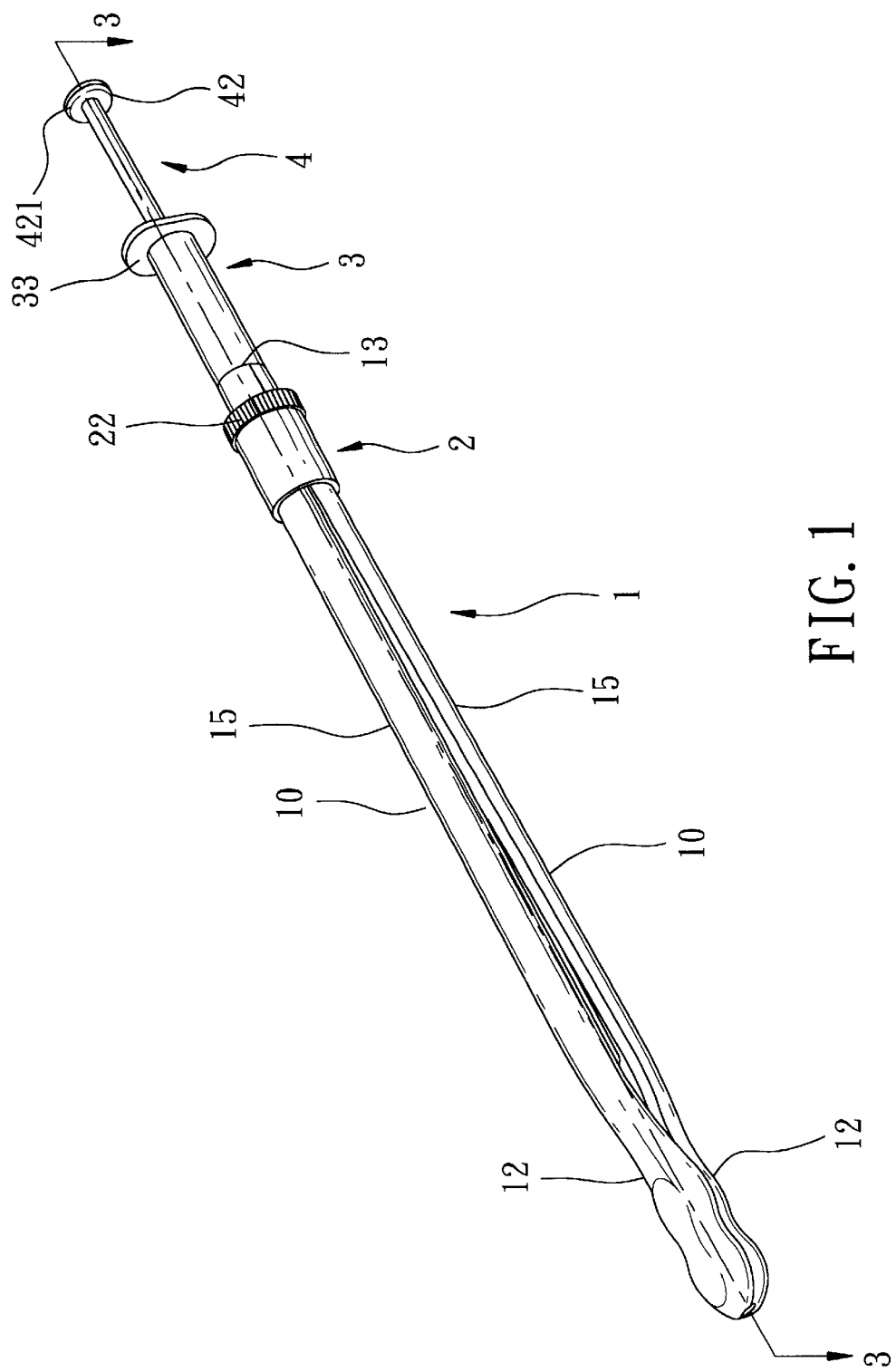
FIG. 1 is a perspective view of the preferred embodiment of a vaginal suppository delivery device according to the present invention.
Figure 2:
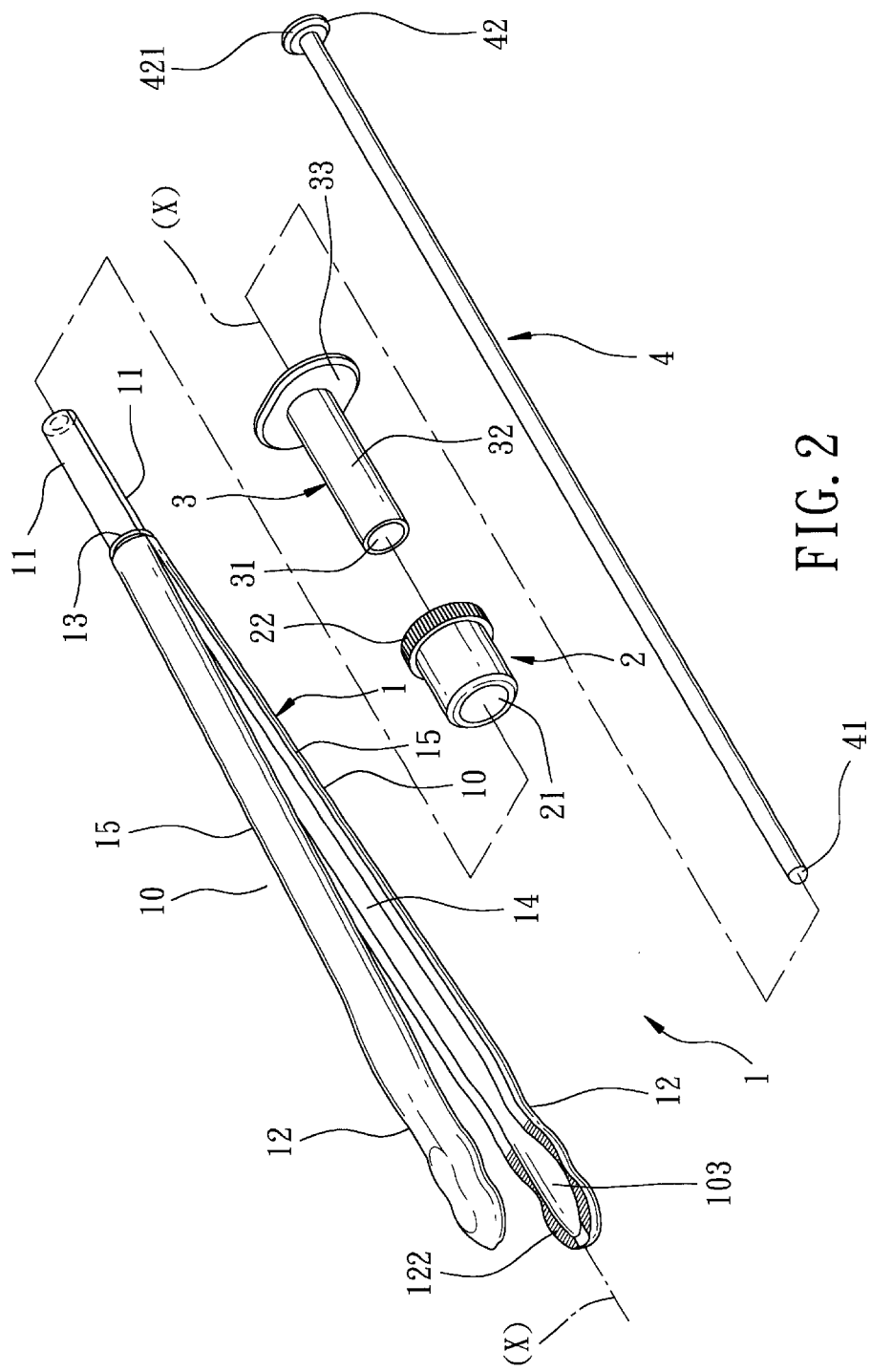
FIG. 2 is an exploded perspective view of the preferred embodiment.
Figure 3:
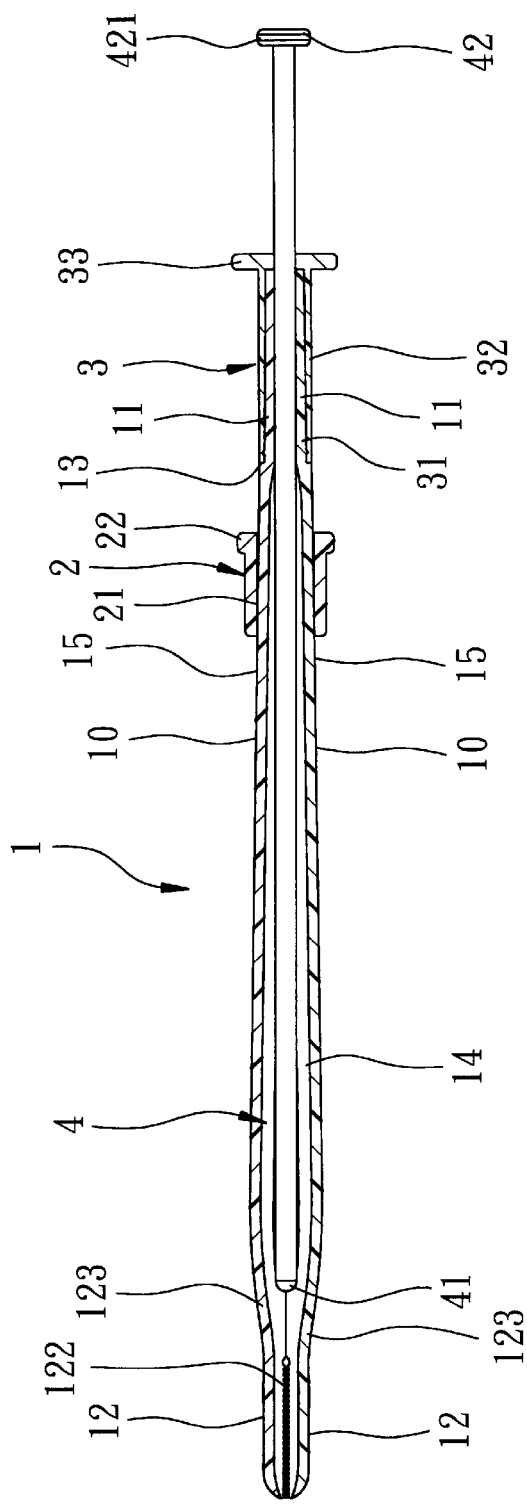
FIG. 3 is an assembled sectional schematic view of the preferred embodiment, taken along line 3—3 of FIG. 1.
Figure 4:
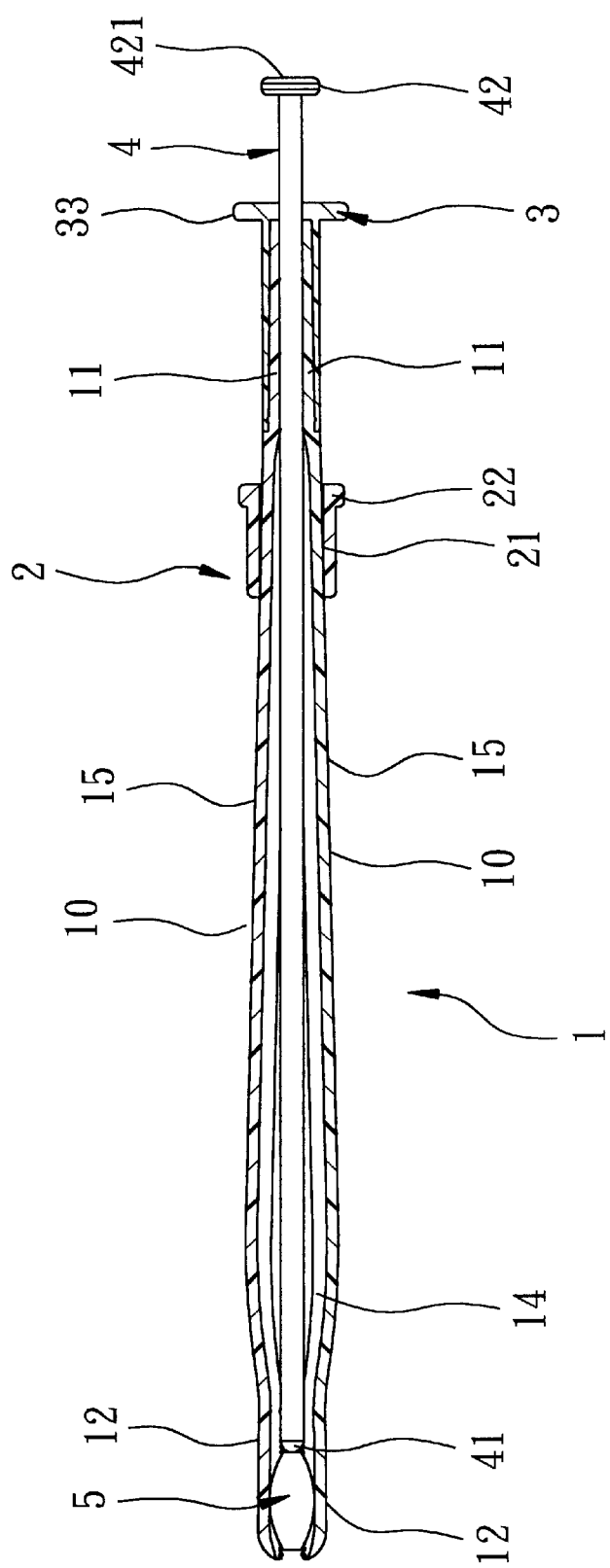
FIG. 4 is another assembled sectional schematic view of the preferred embodiment, illustrating how a suppository is clamped when a sleeve member is moved toward clamp end sections of upper and lower clamp members of a pincer body.

The pincer body 1 has elongate upper and lower clamp members 10 that cooperate to confine a passage 14 extending in an axial direction (X), and has a curved outer contour throughout the length thereof. Each of the upper and lower clamp members 10 has a clamp end section 12, a semi-circular connecting end section 11 opposite to the clamp end section 12, an intermediate section 15 between the clamp and connecting end sections 12, 11, a first inclined transition section 123, and a second transition section 13. The clamp end section 12 of each of the upper and lower clamp members 10 has a shape that is substantially one-half of a peanut hull. The upper and lower clamp members 10 are connected to each other at the connecting end sections 11, and are movable toward and away from each other at the clamp end sections 12. The outer diameter of the upper and lower clamp members 10 at the connecting end sections 11 is smaller than that at the clamp end sections 12. The passage 14 has an oval-shaped drug receiving groove 103 formed in the clamp end sections 12 and adapted for receiving a suppository 5 therein. The clamp end sections 12 of the upper and lower clamp members 10 have knurled surfaces 122 that surround the drug receiving groove 103, and gradually converge in the axial direction (X) away from the connecting end sections 11 to guide insertion of the pincer body 1 into a vaginal cavity. The first inclined transition section 123 of each of the upper and lower clamp members 10 interconnects the intermediate section 15 and the clamp end section 12 such that the passage 14 tapers from the intermediate sections 15 to the clamp end sections 12. The second transition section 13 of each of the upper and lower clamp members 10 interconnects the intermediate section 15 and the connecting end section 11 such that the passage 14 tapers from the intermediate sections 15 to the connecting end sections 11, as best shown in FIGS. 3 and 4.

The sleeve member 2 is sleeved slidably on the pincer body 1, and has a through hole 21 for extension of the pincer body 1 therethrough, and a handling portion 22 formed at one end of the sleeve member 2. In this embodiment, the handling portion 22 is an annular protruding flange formed with knurls so as to facilitate the position adjustment of the sleeve member 2 on the pincer body 1. The sleeve member 2 is movable toward the connecting end sections 11 of the upper and lower clamp members 10 so as to permit the clamp end sections 12 of the clamp members 10 to move away from each other, thereby permitting the suppository 5 to be disposed in the drug receiving groove 103. The sleeve member 2 is further movable toward the clamp end sections 12 of the upper and lower clamp members 10 so as to permit the clamp end sections 12 of the clamp members 10 to move toward each other, thereby clamping the suppository 5 in the drug receiving groove 103.

The positioning tube 3 is sleeved on the connecting end sections 11 of the upper and lower clamp members 10, and has a tubular wall 32 and a first radial outward flange 33 extending from one end of the tubular wall 32. The tubular wall 32 extends in the axial direction (X), and confines a through hole 31 for extension of the connecting end sections 11 of the clamp members 10. In this embodiment, the positioning tube 3 is adhered to the connecting end sections 11 of the clamp members 10 with the use of an adhesive, and an outer surface of the tubular wall 32 is flush with the intermediate sections 15 of the upper and lower clamp members 10 (see FIGS. 3 and 4).

Figure 5:
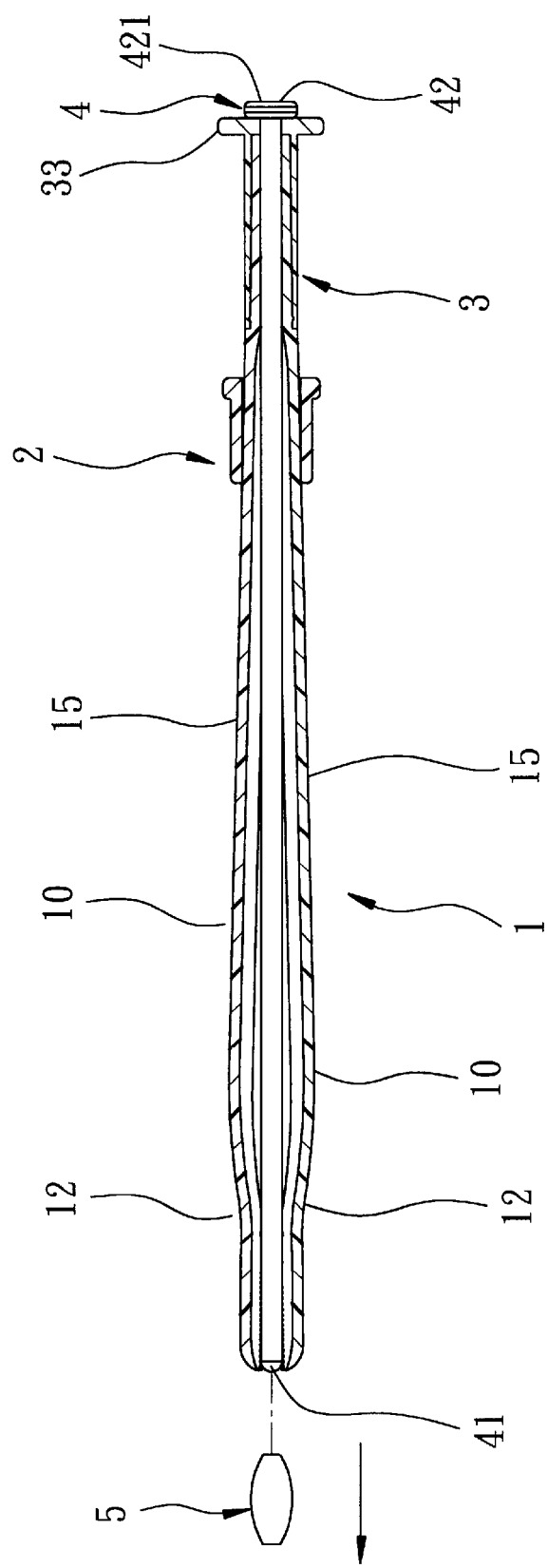
FIG. 5 is yet another assembled sectional schematic view of the preferred embodiment, illustrating how the suppository is pushed out of a drug receiving groove by a push rod.

The elongate push rod 4 is slidably extended into and is movable in the axial direction (X) along the passage 14, and has a drug pushing end 41 and an operating end 42 opposite to the drug pushing end 41 in the axial direction (X). The operating end 42 extends through the passage 14 at the connecting end sections 11 of the upper and lower clamp members 10, and is formed with a second radial outward flange 421 to prevent the operating end 42 from extending into the passage 14, as best shown in FIG. 5.

In use, the push rod 4 is pulled out of the pincer body 1, and the sleeve member 2 is moved toward the positioning tube 3. At this time, the upper and lower clamp members 10 are spaced apart from each other. The suppository 5 is then placed in the drug receiving groove 103, and the sleeve member 2 is adjusted to move toward the clamp end sections 12 of the clamp members 10 until the suppository 5 is clamped by the clamp end sections 12 (see FIG. 4). After ensuring that the suppository 5 is securely clamped, the pincer body 1 can now be inserted into the vaginal cavity. Since the pincer body 1 has a curved outer contour throughout the length thereof, injury to the vaginal cavity can be avoided.

When the pincer body 1 is inserted into the proper depth of the vagina, the operating end 42 of the push rod 4 is pushed until the second radial outward flange 421 abuts against the first radial outward flange 33. At this time, the drug pushing end 41 pushes the suppository 5 to move out of the drug receiving groove 103, thereby delivering the suppository 5 into the vaginal cavity. Note that the drug pushing end 41 of the push rod 4 only reaches the front tips of the clamp end sections 12 and are not extended further, thereby preventing injury to the vagina.

The vaginal suppository delivery device of the present invention can be made of steel or hard plastic. When made of steel, the device has to be sterilized prior to use. When made of plastic, the device can be disposable for sanitation and cleanliness.

The advantages of the vaginal suppository delivery device of the present invention can be summarized as follows:
1. It is convenient to use. The delivery process can be performed by a doctor or by a patient without the need for other tools.
2. In view of the curved outer contour of the pincer body 1, the delivery process is smooth, and pain is not experienced during contact of the device with the vaginal cavity.
3. The first inclined transition sections 123 of the upper and lower clamp members 10 are designed not only to assist the clamping action of the clamp members 10, but also to open the vagina, thereby facilitating the suppository delivery process.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

I claim:

1. A vaginal suppository delivery device comprising:
a pincer body having upper and lower clamp members that cooperate to confine a passage extending in an axial direction, each of said upper and lower clamp members having a clamp end section and a connecting end section opposite to said clamp end section, said upper and lower clamp members being connected to each other at said connecting end sections, and being movable toward and away from each other at said clamp end sections, said passage having a drug receiving groove formed in said clamp end sections and adapted for receiving a suppository therein, said clamp end section of each of said upper and lower clamp members has a shape that is substantially one-half of a peanut hull;
a sleeve member sleeved slidably on said pincer body, said sleeve member being movable toward said connecting end sections of said upper and lower clamp members so as to permit said clamp end sections of said upper and lower clamp members to move away from each other, thereby permitting the suppository to be disposed in said drug receiving groove, said sleeve member being further movable toward said clamp end sections of said upper and lower clamp members so as to permit said clamp end sections of said upper and lower clamp members to move toward each other, thereby clamping the suppository in said drug receiving groove; and
an elongate push rod slidably extended into and movable in the axial direction along said passage, said push rod having a drug pushing end and an operating end opposite to said drug pushing end in the axial direction, said operating end extending through said passage at said connecting end sections of said upper and lower clamp members and being operable so as to enable said drug rushing end to push the suppository to move out of said passage after said pincer body has been inserted into a vaginal cavity, thereby delivering the suppository into the vaginal cavity.

2. The vaginal suppository delivery device as claimed in claim 1, wherein said clamp end sections of said upper and lower clamp members gradually converge in the axial direction away from said connecting end sections to guide insertion of said pincer body into the vaginal cavity.

3. The vaginal suppository delivery device as claimed in claim 1, wherein said clamp end sections of said upper and lower clamp members have knurled surfaces that surround said drug receiving groove.

4. The vaginal suppository delivery device as claimed in claim 1, wherein each of said upper and lower clamp members further has an intermediate section between said clamp and connecting end sections, and an inclined transition section that interconnects said intermediate section and said clamp end section such that said passage tapers from said intermediate sections to said clamp end sections.

5. A vaginal suppository delivery device comprising:

a pincer body having upper and lower clamp members that cooperate to confine a passage extending in an axial direction, each of said upper and lower clamp members having a clamp end section and a connecting end section opposite to said clamp end section, said upper and lower clamp members being connected to each other at said connecting end sections, and being movable toward and away from each other at said clamp end sections, said passage having a drug receiving groove formed in said clamp end sections and adapted for receiving a suppository therein, wherein each of said upper and lower clamp members further has an intermediate section between said clamp and connecting end sections, and a transition section that interconnects said intermediate section and said connecting end section such that said passage tapers from said intermediate sections to said connecting end sections;

a sleeve member sleeved slidably on said pincer body, said sleeve member being movable toward said connecting end sections of said upper and lower clamp members so as to permit said clamp end sections of said upper and lower clamp members to move away from each other, thereby permitting the suppository to be disposed in said drug receiving groove, said sleeve member being further movable toward said clamp end sections of said upper and lower clamp members so as to permit said clamp end sections of said upper and lower clamp members to move toward each other, thereby clamping the suppository in said drug receiving groove;

a positioning tube sleeved on said connecting end sections of said upper and lower clamp members and having an outer surface flush with said intermediate sections of said upper and lower clamp members; and an elongate push rod slidably extended into and movable in the axial direction along said passage, said push rod having a drug pushing end and an operating end opposite to said drug pushing end in the axial direction, said operating end extending through said passage at said connecting end sections of said upper and lower clamp members and being operable so as to enable said drug pushing end to push the suppository to move out of said passage after said pincer body has been inserted into a vaginal cavity, thereby delivering the suppository into the vaginal cavity.

6. The vaginal suppository delivery device as claimed in claim 1, wherein said pincer body has a curved outer contour throughout the length thereof.

7. A The vaginal suppository delivery device, comprising:

a pincer body having upper and lower clamp members that cooperate to confine a passage extending in an axial direction, each of said upper and lower clamp members having a clamp end section and a connecting end section opposite to said clamp end section, said upper and lower clamp members being connected to each other at said connecting end sections, and being movable toward and away from each other at said clamp end sections, said passage having a drug receiving groove formed in said clamp end sections and adapted for receiving a suppository therein;

a sleeve member sleeved slidably on said pincer body and being formed with a knurled handling portion, said sleeve member being movable toward said connecting end sections of said upper and lower clamp members so as to permit said clamp end sections of said upper and lower clamp members to move away from each other, thereby permitting the suppository to be disposed in said drug receiving groove, said sleeve member being further movable toward said clamp end sections of said upper and lower clamp members so as to permit said clamp end sections of said upper and lower clamp members to move toward each other, thereby clamping the suppository in said drug receiving groove; and an elongate rush rod slidably extended into and movable in the axial direction along said passage, said push rod having a drug pushing end and an operating end opposite to said drug pushing end in the axial direction, said operating end extending through said passage at said connecting end sections of said upper and lower clamp members and being operable so as to enable said drug pushing end to push the suppository to move out of said passage after said pincer body has been inserted into a vaginal cavity, thereby delivering the suppository into the vaginal cavity.

8. The vaginal suppository delivery device as claimed in claim 1, wherein said operating end of said push rod is formed with a radial outward flange to prevent said operating end from extending into said passage.

* * * * *